US012691099B2

(12) United States Patent
Mahendrabhai et al.

(10) Patent No.: US 12,691,099 B2
(45) Date of Patent: Jul. 28, 2026

(54) ORAL FORMULATIONS OF EDARAVONE AND METHOD OF MANUFACTURING THEREOF

(71) Applicant: BDR PHARMACEUTICALS INTERNATIONAL PRIVATE LIMITED, Mumbai (IN)

(72) Inventors: Shah Dharmesh Mahendrabhai, Mumbai (IN); Badiger Aravind Manappa, Panchmahals (IN); Patel Bhavesh Naginbhai, Panchmahals (IN); Choksi Rakshit Kentanbhai, Panchmahals (IN); Patil Mayurkumar Purshot-Tambhai, Panchmahals (IN); Shah Jigar Atulkumar, Panchmahals (IN); Trivedi Madhavkumar Dilipbhai, Panchmahals (IN)

(73) Assignee: BDR PHARMACEUTICALS INTERNATIONAL PRIVATE LIMITED, Mumbai (IN)

( * ) Notice: Subject to any disclaimer, the term of this patent is extended or adjusted under 35 U.S.C. 154(b) by 1167 days.

(21) Appl. No.: 17/636,719

(22) PCT Filed: Jul. 17, 2020

(86) PCT No.: PCT/IN2020/050614
§ 371 (c)(1),
(2) Date: Feb. 18, 2022

(87) PCT Pub. No.: WO2021/009775
PCT Pub. Date: Jan. 21, 2021

(65) Prior Publication Data
US 2022/0409588 A1 Dec. 29, 2022

(30) Foreign Application Priority Data
Jul. 18, 2019 (IN) ............................. 201921028874

(51) Int. Cl.
*A61K 31/4152* (2006.01)
*A61K 9/00* (2006.01)
(Continued)

(52) U.S. Cl.
CPC ........ *A61K 31/4152* (2013.01); *A61K 9/0053* (2013.01); *A61K 47/02* (2013.01);
(Continued)

(58) Field of Classification Search
CPC .. A61K 31/4152; A61K 9/0053; A61K 47/26; A61K 47/36; A61K 9/0095; A61K 9/10
See application file for complete search history.

(56) References Cited

U.S. PATENT DOCUMENTS 6,933,310 B1 8/2005 Ikeda

FOREIGN PATENT DOCUMENTS

| | | | |
|---|---|---|---|
| CN | 1440749 | * | 9/2003 |
| CN | 1449754 A | | 10/2003 |

(Continued)

OTHER PUBLICATIONS

English translation of CN1440749 (Year: 2003).*
(Continued)

*Primary Examiner* — San Ming R Hui
(74) *Attorney, Agent, or Firm* — Kramer & Amado, P.C.

(57) ABSTRACT

The present invention relates to oral suspension dosage form of Edaravone. The invention also relates to provide patient-compliant, economical and technically advanced dosage form over existing marketed dosage form. Moreover, the solubility and stability of the patient compliant Edaravone formulation, prepared as per the present invention, is proven higher when compared to prior art inventions. Furthermore, the present invention also provides a suspension composition prepared by a process which is relatively simple, easy
(Continued)

to commercially manufacture, and functionally reproducible.

9 Claims, 1 Drawing Sheet

(51) Int. Cl.
*A61K 47/02* (2006.01)
*A61K 47/10* (2017.01)
*A61K 47/14* (2017.01)
*A61K 47/26* (2006.01)
*A61K 47/36* (2006.01)

(52) U.S. Cl.
CPC .............. *A61K 47/10* (2013.01); *A61K 47/14* (2013.01); *A61K 47/26* (2013.01); *A61K 47/36* (2013.01)

(56) References Cited

FOREIGN PATENT DOCUMENTS

| | | | |
|---|---|---|---|
| CN | 102349893 | A | 2/2012 |
| CN | 107773545 | A | 3/2018 |
| DE | 473214 | | 12/1929 |
| WO | 2009067343 | A1 | 5/2009 |
| WO | 2012019381 | A1 | 2/2012 |
| WO | 2017157350 | A1 | 9/2017 |
| WO | 2018133957 | A1 | 7/2018 |
| WO | 2018134243 | A1 | 7/2018 |
| WO | 2019088881 | A1 | 5/2019 |
| WO | 2019213333 | A1 | 11/2019 |

OTHER PUBLICATIONS

Waterman et al., Pharmaceutical Development and Technology, 7(1), 1-32 (2002) (Year: 2002).*
Cruz, Pharmacy and Therapeutics, vol. 43, No. 1, Jan. 2018 (Year: 2018).*
Chu et al., Arch Pharm Res vol. 35, No. 7, 1187-1195, 2012 (Year: 2012).*
Toshiaki Sato, et al., Pharmacology 2010(85); p. 88-94.
Parikh et al., International Journal of Pharmaceutics, 2016(515); p. 490-500.
Parikh et al., Drug Delivery 2017; 24(1); p. 962-978.

* cited by examiner

ORAL FORMULATIONS OF EDARAVONE AND METHOD OF MANUFACTURING THEREOF

FIELD OF THE INVENTION

The present invention relates to oral liquid formulation of Edaravone as a suspension. Further, the present invention relates to providing an economical and technically advanced dosage form over existing parenteral dosage form.

BACKGROUND OF THE INVENTION

Edaravone (CAS: 89-25-8) is a member of substituted 2-pyrazolin-5-one chemical moiety. Edaravone is chemically known as [3-methyl-1-phenyl-2-pyrazolin-5-one] and is represented structurally as below:

(I)

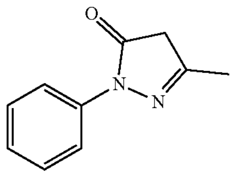

EDARAVONE

Edaravone is disclosed earlier during 1925 in DE473214. The said German patent discloses a process for the preparation of 1-phenyl-3-methylpyrazolone by the oxidation of 1-phenyl-3-methylpyrazolidone in aqueous hydrochloric acid solution and in the presence of oxygen-transferring metal salts, characterized by the use of oxygen or oxygen-containing metal salts gases as oxidizing agents.

Edaravone is marketed presently under the brand name "RADICAVA®" in United States. This intravenous infusion is indicated for the treatment of amyotrophic lateral sclerosis (ALS). The recommended dosage for Edaravone is 60 mg which is administered as an intravenous infusion over 60 minutes. Prior to US approval, Mitsubishi Tanabe Pharm Corp. (Osaka, Japan) launched Edaravone under the brand name "RADICUT®" in Japan as world's first neurovascular protective drug.

The recommended dose of Edaravone is 60 mg, which should be administered in the form of two consecutive infusion bags containing 60 mg of Edaravone, i.e. 30 mg per each infusion bag over a period of 60 minutes. Each 100 ml infusion bag of RADICAVA® contains Edaravone, L-cysteine hydrochloride hydrate and sodium bisulfate. The pH of the formulation is adjusted with phosphoric acid and sodium hydroxide and the isotonicity is maintained by adding sodium chloride. The dosing regimen of Edaravone consist of 2 cycles. Cycle 1 includes an initial treatment cycle with daily dosing for 14 days; followed by a 14-day drug-free period. Subsequent treatment cycles (cycles 2 to 6) are provided with daily dosing for 10 days out of 14-day periods; followed by 14-day drug-free periods.

Edaravone is prone to oxidation from environmental oxygen. Therefore, Edaravone is supplied in single-dose polypropylene bags, each overwrapped with polyvinyl alcohol (PVA). Further, secondary packaging contains an oxygen absorber with oxygen indicator, which should be pink to reflect appropriate oxygen levels. The oxygen indicator will turn blue or purple if the oxygen has exceeded acceptable levels.

U.S. Pat. No. 6,933,310 claims a method for treating motor neuron diseases, amyotrophic lateral sclerosis (ALS), consisting essentially of administering an effective amount of Edaravone or a physiologically acceptable salt thereof to a patient.

CN1241565C discloses a freeze-dried pharmaceutical composition of Edaravone to facilitate storage and transport. As per this Chinese patent, Edaravone powder is suspended in water for injection and alkaline material followed by addition of other scaffolds agent to prepare lyophilized dosage form. However, the said invention is not considered as friendly for long-term treatment from the patient compliance point of view. Therefore, there is a need for a patient compliant invention.

WO2009/067343 discloses an emulsion formulation of wherein alcohol, chelating agent and reducing agents are absent. Further, the emulsifier is chosen from egg-yolk phospholipid or soybean phospholipid. However, during long-term storage, poor stability of this liquid emulsion dosage form is a hurdle and requires a novel stable dosage form.

The said patent discloses stability data for about 3 months, only. Hence, the inventors of the present invention felt that there is an unmet need for the pharmaceutical composition of Edaravone which is stable and in oral form to provide more patient compliance.

WO2012/019381 discloses an oral pharmaceutical composition containing inclusion complex of Edaravone and cyclodextrin. This patent comprises mixing Edaravone with cyclodextrin into water for 1 to 2 h. More contact time with water forces Edaravone to hydrolyze. This invention does improve solubility of Edaravone; however, fails to reduce inherent oxidation of Edaravone. Therefore, there is requirement of a novel invention that yields better solubility with significant stability of Edaravone in the oral dosage form. This patent has failed to report the stability data and hence, it proves that the prepared solid pharmaceutical composition for Edaravone is not stable.

WO2017/157350 discloses a lipid-based drug delivery system comprising Edaravone or a pharmaceutically acceptable salt thereof. A solid dispersion comprises Edaravone and a polymeric carrier. However, preparing solid dispersion of Edaravone needs reduction in particle size of API and reduction in particle size yield larger surface area to Edaravone.

Thereby, producing higher chance of oxidation to Edaravone due to larger surface area of particles. Therefore, this invention also fails to minimize oxidative effect on Edaravone. Absence of stability data in the patent indicates that lipid-based compositions of Edaravone are not stable.

WO2018/133957 claims a solid water-dispersible pharmaceutical composition comprising of dispersing the pharmaceutical composition into an aqueous liquid to produce an enterally administrable liquid containing at least 0.5 grams of the pharmaceutical composition and at least 0.3 g/l of Edaravone, followed by enterally administering the liquid to a human patient in an amount providing a dose of 30-300 mg Edaravone. The said pharmaceutical composition comprising 2-50 wt. % of Edaravone and 3-50 wt. % of water-soluble alkalizing agent. This patent has failed to report the stability data and hence, it proves that the prepared solid water-dispersible pharmaceutical composition for Edaravone is not stable.

WO2018/134243 discloses a liquid pharmaceutical composition which is a monophasic aqueous solution of non-complexed Edaravone that comprise of at least 75 wt. % water and 0.2-9 mg/ml of Edaravone, wherein the treatment comprises oral or gastric administration of 10-250 ml of the liquid pharmaceutical composition to provide 30-300 mg Edaravone. This patent has failed to report the stability data and hence, it proves that the prepared liquid composition for Edaravone is not stable.

Toshiaki Sato et. al. (*Pharmacology* 2010(85); p. 88-94) describes pharmacokinetics of Edaravone using Edaravone/hydroxypropylβ-cyclodextrin complex solution, including L-cysteine (L-Cys) and sodium hydrogen sulfite (SHS). This study suggested that L-Cys and SHS were useful for the oral mucosal and rectal administration of Edaravone. These types of compositions are already reported in the previous inventions and hence, face similar kind of difficulties of stability as discussed during WO2012/019381.

Parikh et al. (*International Journal of Pharmaceutics,* 2016(515); p. 490-500) discuss the development of an oral delivery system of Edaravone. The Novel Oral Delivery System (NODS) of Edaravone that is made up of a mixture of Labrasol and an acidic aqueous system that was optimized on the basis of a solubility and stability study. It was found that the oral bioavailability of the NODS delivery system was 5.7 times higher than that of an Edaravone suspension containing 30 mg/mL Edaravone and 0.5% of sodium carboxymethyl cellulose. Higher amount of Labrasol in oral formulation increases gastric disturbances in patient and hence, patient compliance is reduced. Hence, the inventors of the present invention have noted that there is a need for the oral pharmaceutical composition of Edaravone which is stable and not produces the side effects like gastric disturbances.

Parikh et al. (*Drug Delivery* 2017; 24(1); p. 962-978) describe a study that aimed at enabling oral use of Edaravone by developing a lipid-based nanosystem (LNS). The components of LNS including oil, surfactants, and co-surfactants were selected based on their potential to maximize the solubilization in gastrointestinal (GI) fluids, reduce its glucuronidation and improve transmembrane permeability. A liquid LNS (L-LNS) in the form of a micro-emulsion was prepared, comprising Capryol™ PGMC (Oil), Cremophor® RH 40: Labrasol®: TPGS 1000 (1:0.8:0.2) (Surfactant) and Transcutol® P (Co-surfactant). It was found that the oral bioavailability of the L-LNS was almost 11 times higher than that of an Edaravone suspension containing 30 mg/mL Edaravone and 0.5% of sodium carboxymethyl cellulose. Due to presence of so many expensive ingredients, final cost of such formulation increases to very high level. Hence, the inventors of the present invention noted that there is an unmet need of oral pharmaceutical composition of Edaravone which is stable as well as cost-effective to the patients and thereby making it affordable and patient compliant.

Also, it may be noted that the efficacy of Edaravone has seen an undisputed success since its inception in the therapeutic category of stroke management. Edaravone per se has wide applicability and has potential to be used for more therapeutic indications. The injectable dosage form has been a limiting factor in case of increased use of this product. Importantly, developing an oral dosage form of Edaravone is a challenging process due to its less soluble and less permeable (BCS Class-IV product) nature. Further, an injectable dosage form has inherent difficulty in terms of its usage post hospitalization. Apart from all these, Edaravone is also quite sensitive to hydrolysis and oxidation and thereby making an oral formulation is more difficult. Above limitations were identified quite effectively by the inventors of the present invention and hence, a stable-efficacious oral suspension dosage form has been developed to meet the identified needs in the prior-art publications.

The present invention discloses the administration of Edaravone in an oral suspension form that does not use sophisticated techniques and is economically affordable compared to parenteral dosage form. Further, the formulated oral liquid suspension dosage form prepared as per the present invention provides greater stability when compared with marketed Edaravone liquid formulation. Moreover, the oral route is the preferred one for administration in patients with chronic neurodegenerative diseases. In addition, medical practitioners also prefer oral dosage form over injectable dosage forms due to advantages like ease of administration, increased patient compliance, reduced the need for the hospital stay.

A suspension is a heterogeneous mixture that contains solid particles sufficiently large for sedimentation. The suspended particles may be visible to the naked eye which is usually larger than 1 micrometer. A suspension is a heterogeneous mixture in which the suspended particles do not dissolve, although they remain suspended throughout the bulk of the liquid medium. Generally, the solid part is dispersed through mechanical agitation using suspending agents. In contrast, solution have dissolved and homogeneously mixed solute which does not exist as a solid.

The present invention incorporates Edaravone with stabilizers which reduce the oxidation of Edaravone. Further, smaller particle size of suspension increases the solubility of Edaravone by providing better dissolution profile. Moreover, the present invention resulted in achieving higher stability of Edaravone as comparing to marketed parenteral dosage form. Moreover, the solubility and stability of the patient compliant Edaravone formulation, prepared as per the present invention, is proven higher when compared to prior art inventions.

Further, the present invention provides a suspension composition prepared by a process which is relatively simple, easy to commercially manufacture, and functionally reproducible. Additionally, a suspension composition of the present invention is also able to incorporate two or more active ingredients.

SUMMARY OF THE INVENTION

Despite of extensive research on Edaravone as reported in prior-art publications, an oral composition of Edaravone is not available commercially around the globe. It has thus been unmet need to develop a patient compliant oral composition for Edaravone with good stability.

Accordingly, the present invention provides an oral composition of Edaravone preferably as suspension dosage form with pharmaceutically acceptable excipients and method of preparation thereof.

The prime objective of the present invention is that the pharmaceutical composition establishes a dual release pattern owing to kind of solubilizes used in the formulation and thereby producing an immediate burst absorption followed by delayed absorption.

In one general aspect, a pharmaceutical composition as per the present invention is in the form of liquid formulation.

In yet another aspect, a pharmaceutical composition as per the present invention comprises Edaravone and one or more pharmaceutically acceptable excipients wherein the composition is in the form of a suspension.

In yet another general aspect, a pharmaceutical composition as per the present invention comprises Edaravone and one or more pharmaceutically acceptable excipients wherein the composition is in the form of an oral suspension.

In one embodiment of the present invention, wherein the active ingredient incorporated in the pharmaceutical composition comprises $D_{90}$ of particle size in the range of 2 to 100 microns, preferably, $D_{90}$ in the range of 2 to 80 microns.

In one of the embodiments, the pharmaceutical composition manufactured as per the present invention is a suspension.

In yet another embodiment of the present invention, wherein the pharmaceutical composition manufactured is having particle size ranging from nanometer to micrometer, which results in to enhanced in-vitro dissolution profile.

Another embodiment according to the present invention, wherein the formulated product manufactured is having particle size ranging from nanometer to micrometer, which results in to enhanced in-vitro dissolution profile about 80% to 95%.

Additional embodiment according to the present invention, wherein the formulation manufactured is having particle size ranging from nanometer to micrometer, which results in to enhanced bio-absorption about 40% to 90%.

In yet another embodiment of the present invention, wherein the pharmaceutical composition manufactured by number of stages in manufacturing process including homogenization, sonication, mixing and/or evaporation by spray drying.

Additional embodiment according to the present invention is that the formulated product is a stabilized homogenous suspension.

In yet another embodiment of the present invention, wherein pH of the pharmaceutical composition is in the range of 2 to 6.5, more preferably in the range of 3.0 to 4.5.

In another general aspect, a pharmaceutical composition as per the present invention comprises Edaravone or pharmaceutically acceptable salt thereof.

In another embodiment of the present invention, wherein the carrier molecules present in the pharmaceutical composition enhances absorption of Edaravone owing to their optimum hydrophilic and hydrophobic properties.

In other embodiments of the present invention, wherein absorption of the active molecules is facilitated by passive absorption due to presence of adjuvant lipidic excipients.

Embodiments of the pharmaceutical composition may include Edaravone as an active ingredient with one or more selected from pharmaceutically acceptable excipients like diluent vehicles, stabilizers/anti-oxidants, suspending/thickening agents, chelating/complexing agents, solubility enhancing agents, permeability enhancers, preservatives, glidants, active carriers, sweeteners, anti-caking agents, wetting agents, preservatives, buffering agents, flavoring agents and the like.

In another embodiment of the present invention, wherein Edaravone is having particle size in the range from 800 nm to 10000 nm, more preferably 2000 nm to 8000 nm.

In another embodiment of the present invention, to minimize oxidation of the sensitive material it is also desirable to remove headspace oxygen and moisture or both from the sealable vessel as quickly as possible, purging of inert gas is carried out using argon, helium or nitrogen, or mixtures thereof.

In another embodiment of the present invention, pharmaceutical composition is in the form of an oral suspension comprising:

a) one or more pharmaceutically acceptable stabilizers and/or anti-oxidants as part-A;
b) Edaravone with one or more pharmaceutically acceptable surfactant, co-surfactant, permeability enhancer and anti-foaming agent to produce drug part-B;
c) one or more pharmaceutically acceptable suspending or thickening agents as part-C;
d) one or more pharmaceutically acceptable sweetening agents, flavouring agents and colouring agents as part-D;
e) one or more pharmaceutically acceptable liquid vehicles for suspension as part-E.

In one embodiment, process for preparation of an oral pharmaceutical composition as per the present invention comprising following steps:

a) dissolving anti-oxidants and/or stabilizers in purified water to prepare part-A;
b) dissolving surfactant, co-surfactant, micronized Edaravone along with permeability enhancer and anti-foaming agent to obtain a suspension;
c) dissolving suspending agent and thickening agent in above prepared suspension to provide appropriate viscosity;
d) adding sweetening agent in above-prepared suspension and mixing the same through vortex or high-speed homogenizer or mechanical or sonicated or shear stress to obtain a uniform nano-suspended formulated dosage form;
e) making-up volume of the above nano-suspension with aqueous vehicle.

The details of one or more embodiments of the invention are set forth in the description below. Other features of the invention will be apparent from the description.

DETAILED DESCRIPTION OF THE INVENTION

Figure 1A:
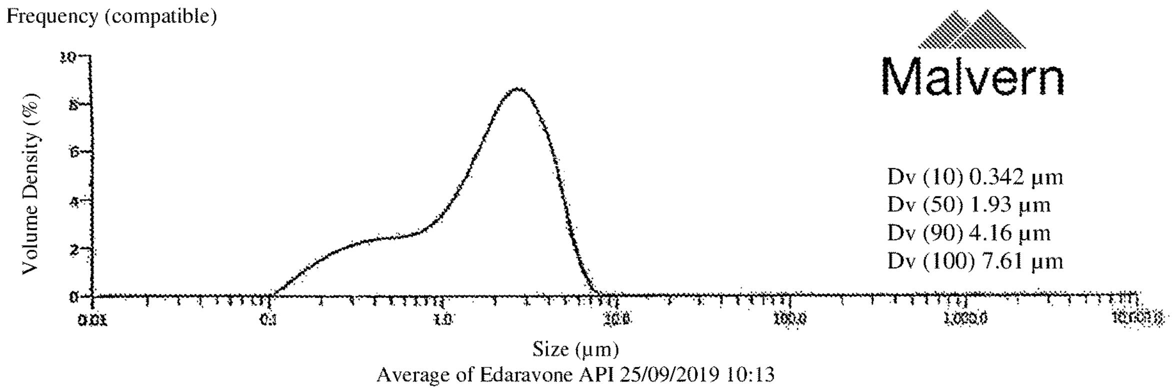
FIG. 1A: illustrates particle size distribution graph for Edaravone used in the present invention.
Figure 1B:
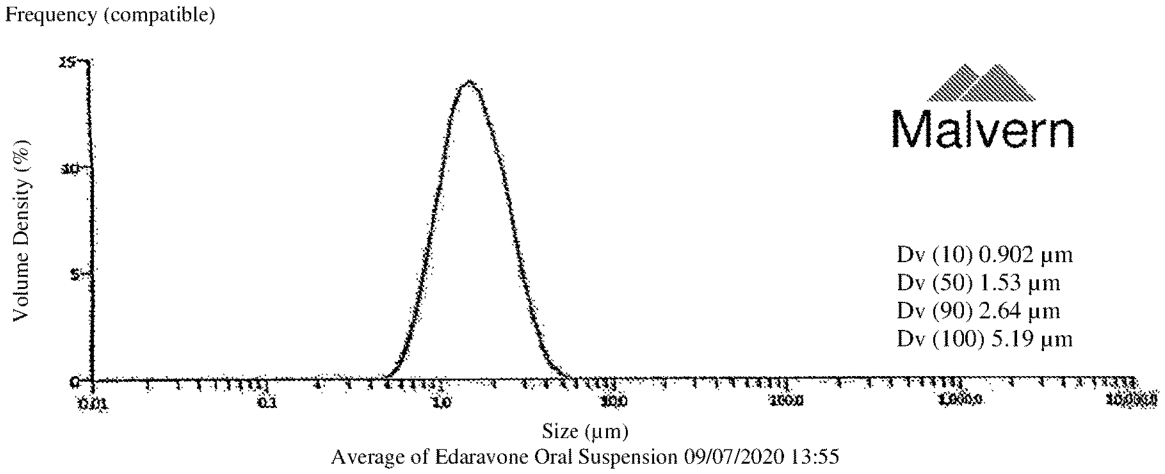
FIG. 1B: illustrates particle size distribution graph for Edaravone oral suspension prepared as per the present invention.

The present invention will now be disclosed by describing certain preferred and optional embodiments, to facilitate various aspects thereof.

Edaravone, chemically known as, 3-methyl-1-phenyl-2-pyrazolin-5-one, is a small lipophilic molecule with molecular weight 174.203 g/mol with a solubility of 25 μg/ml.

Edaravone is considered a Bio-pharmaceutics Classification System (BCS) Class IV drug substance due to its poor solubility in water and lower lipid permeability. The mean terminal elimination half-life of Edaravone is 4.5 to 6 h.

In accordance with the present invention, a pharmaceutical composition of Edaravone comprising of Edaravone as an active ingredient with pharmaceutically acceptable excipients.

The term "pharmaceutically acceptable excipients" as used herein, refers to excipients those are routinely used in pharmaceutical compositions. The pharmaceutically acceptable excipients may comprise of diluent vehicles, stabilizers/anti-oxidants, suspending/thickening agents, chelating/complexing agents, solubility enhancing agents, preservatives, glidants, sweeteners, anti-caking agents, wetting agents, preservatives, buffering agents, flavoring agents and combinations thereof.

At the time of preparation of the dosage form, the excipients of oral suspension are mainly divided into following parts according to their uses in the manufacturing process (A) drug part, (B) stabilizers, (C) suspending/thickening agents, (D) Sweetening & flavoring agents, and (E) diluent vehicle. The list of excipients used are listed in tables below although it is not limited to the said excipients.

Suitable diluent vehicle may include one or more from aqueous vehicle, sugar, methylcellulose gel, citric acid, sucrose, sorbitol solution, sodium carboxy methylcellulose solution, xanthan gum solution, non-aqueous vehicle like refined fractionated coconut oil, hydrogenated castor oil, lecithin, aluminum stearate and the like.

The inventors of the present invention during development of the present invention noted that it was difficult to stabilize Edaravone for a long period time. Edaravone has tendency to easily decompose by oxidation in the aqueous solution when compared to the powdered form. In consideration of such properties, additionally the suspension can be further stabilized by using Antioxidants. The Anti-oxidant agents may be present in a concentration of about 5 to about 15 mg/ml, more preferably about 7 to about 12 mg/ml, most preferably about 10 mg/ml.

Suitable stabilizers or anti-oxidants may include one or more from citric acid, butylated hydroxytoluene, butylated hydroxy anisole, sodium bisulphite, ascorbic acid, L-cysteine, magnesium bisulfite, sodium metabisulfite, tocopherol, ubiquinol, β-carotenes, uric acid, lipoic acid, propyl gallate, thiourea, glutathione and the like.

It is common in the art that surfactant reduces the interfacial tension. The inventors of the present invention used surfactant in such a way that it is adsorbed on the particles and flocculation was minimized because of natural repulsion between positively and negatively charged particles. The inventors of the present invention noted that some particles which do not have sufficient surface energy come together and are forming large particles. To overcome that difficulty, the inventors of the present invention have added the suspending agents. The suspending agents or thickening agents increase the viscosity of the continuous phase so that the particles remain suspended for a sufficient longer time. These structured vehicles entrapped the particle and reduces the sedimentation of particles. Although, these structured vehicles reduce the sedimentation of particles.

Suitable suspending or thickening agents may include one or more from sodium alginate, methylcellulose, hydroxyethyl cellulose, hydroxypropyl methylcellulose, carboxymethyl cellulose, sodium carboxymethyl cellulose, microcrystalline cellulose, acacia, tragacanth, xanthan gum, bentonite, carbomer, carrageen, gelatin and the like.

The inventors of the present invention observed microbial-growth in the formulation prepared at the longer storage. Hence, it was necessary to stabilize the suspension against wide range of micro-organisms. Hence, preservative those are non-toxic and compatible with other excipients were used in this composition.

Suitable preservative may include one or more from propylene glycol, disodium EDTA, benzalkonium chloride, benzoic acid, butyl paraben, methyl paraben, propyl paraben, sodium benzoate, alkali metal bisulfite and the like. As per the present invention, alkali metal bisulfite may be selected from sodium bisulfite, potassium bisulfite and combinations thereof. Most preferably, the alkali metal bisulfite employed in the suspension is sodium bisulfite.

Suitable anti-caking agents may include one or more from colloidal silicon dioxide, tribasic calcium phosphate, magnesium trisilicate, starch and the like.

It is known in the art that the wetting agents or substances reduce the interfacial tension between the solid particle and liquid phase. These substances are adsorbed at the solid-liquid interface, in such way that the affinity of the particles for the surrounding medium is increased and intraarticular forces are decreased. The particles, even high density, float on the surface of the liquid until the layer of air is displaced completely. The use of wetting agent allows removing this air from the surface and to easy penetration of the vehicle into the pores.

Suitable wetting agents may include one or more from the group comprising anionic, cationic, nonionic, or zwitterionic surfactants, or combinations thereof. Suitable examples of wetting agents are sodium lauryl sulphate, cetrimide, polyethylene glycols, polyoxyethylene-polyoxypropylene block copolymers such as poloxamers, polyglycerin fatty acid esters such as decaglyceryl monolaurate and decaglyceryl monomyristate, sorbitan fatty acid esters such as sorbitan monostearate, polyoxyethylene sorbitan fatty acid esters such as polyoxyethylene sorbitan monooleate, polyethylene glycol fatty acid esters such as polyoxyethylene monostearate, polyoxyethylene alkyl ethers such as polyoxyethylene lauryl ether, polyoxyethylene castor oil and the like.

Suitable buffering agents may include one or more from the group comprising citric acid, sodium citrate, sodium phosphate, potassium citrate, acetate buffer and the like.

Suitable permeability enhancers may include one or more from the group comprising alcohols, Polyols, short chain glycerides, amines, amides, cyclodextrins, fatty acids, pyrrolidines, azones, sulfoxides, surfactants, terpenes and the like.

Suitable active carrier molecules may include one or more from the group comprising piperine and the like.

Suitable surfactants or co-surfactants may include one or more from anionic, cationic, non-ionic or amphoteric surfactants. Non-limiting examples of surfactants may include polyoxyethylene-polyoxypropylene co-polymers and block co-polymers, ethoxylated cholesterins, vitamin derivatives, e.g. vitamin E derivatives such as tocopherol polyethylene glycol succinate (TPGS), sodium dodecylsulfate or sodium lauryl sulfate; a bile acid or salt thereof, for example cholic acid, glycolic acid or a salt; and the like.

Suitable flavoring agents may include one or more from the group consisting of peppermint, grapefruit, orange, lime, lemon, mandarin, pineapple, strawberry, raspberry, mango, passion fruit, kiwi, apple, pear, peach, apricot, cherry, grape, banana, cranberry, blueberry, black currant, red currant, gooseberry, lingon berries, cumin, thyme, basil, camille, valerian, fennel, parsley, chamomile, tarragon, lavender, dill, bargamot, *salvia*, aloevera balsam, spearmint, piperine, *eucalyptus*, and the like.

Suitable chelating or complexing agents may include one or more from the group comprising cyclodextrin, ethylenediamine tetra acetic acid or derivatives/salts thereof, e.g. disodium edetate, dihydroxyethyl glycine, glucamine, citric acid, tartaric acid, gluconic acid, phosphoric acid and the like.

Suitable solubility enhancing agents may include one or more from the group comprising surfactants such as (1) non-ionic e.g., polyoxyethylene sorbitan fatty acid esters, sorbitan esters, polyoxyethylene ethers, (2) anionic e.g., sodium lauryl sulfate, sodium laurate, dialkyl sodium sulfosuccinates, particularly bis-(2-ethylhexyl) sodium sulfosuccinate, sodium stearate, potassium stearate, and sodium oleate, (3) cationic e.g., benzalkonium chloride and bis-2-hydroxyethyl oleyl amine, and (4) zwitterionic/amphoteric surfactants; fatty alcohols such as lauryl, cetyl, and stearyl alcohols; glyceryl esters such as the naturally occurring mono-, di-, and tri-glycerides; fatty acid esters of fatty alcohols and other alcohols such as propylene glycol, polyethylene glycol; sucrose; polymers e.g., poloxamers, polyvinylpyrrolidones, glycerides e.g., triacetin, glyceryl monocaprylate, glyceryl monooleate, glyceryl monostearate; diethylene glycol monoethyl ether; and the like.

Suitable anti-foaming agents used in the present invention may include one or more from the group comprising such as methylated linear siloxsane polymers end blocked with trimethylsiloxyl units such as dimethicone and simethicone, as well as mixtures of dimethicone with an average chain length of 200 to 250 dimethyl siloxane units and silica gel. The effective amount of anti-foaming agents is an amount sufficient to provide a concentration of about 4 mg/ml to about 8 mg/ml, preferably about 6 mg/ml.

Suitable viscosity enhancers include used in the present invention may include one or more from the group comprising such as Xanthan gum, liquid sugars, starches, celluloses and mixtures thereof. The xanthan gum is present in an amount of about 1 mg/ml to about 5 mg/ml, and more preferably the xanthan gum is present in an amount of about 3.7 mg/ml. preferably, most common suspending agents are aqueous biological polymers including methylcellulose (MC), sodium carboxy methyl cellulose (CMC), and hydroxy propyl methyl cellulose (HPMC). A range of viscosity enhancers are used with different molecular weights in range of 5 to 20 mg/ml. More preferably the HPMC E15 is present in an amount of about 10 mg/ml. The viscosity enhancers of the present invention facilitate suspension of the formulation after constitution with minimum agitation and prevent rapid settling and caking of the suspension over time.

The prime objective of the present invention is that the pharmaceutical composition establishes a dual release pattern owing to kind of solubilizes used in the formulation and thereby producing an immediate burst release followed by maintenance release.

One embodiment of the present invention may include a pharmaceutical composition comprising about 0.1 mg to 500 mg of Edaravone with pharmaceutically acceptable excipients.

Another embodiment of the present invention includes a pharmaceutical composition comprising Edaravone with pharmaceutically acceptable excipients but devoid of pH adjusting agents and isotonicity agents.

In other embodiment of the present invention, Edaravone is present in an amount ranging from 1 mg/ml to 90 mg/ml.

In one embodiment of the present invention, wherein the active ingredient incorporated in the pharmaceutical composition comprises $D_{90}$ of particle size in the range of 2 to 100 microns, preferably, $D_{90}$ in the range of 2 to 80 microns.

In another embodiment of the present invention, wherein Edaravone is having particle size in the range from 800 nm to 10000 nm, more preferably 2000 nm to 8000 nm.

In a preferred embodiment, $D_{100}$ of particle size of Edaravone is less than 8000 nm or 8 microns.

In one of the embodiments, the pharmaceutical composition manufactured as per the present invention is nano-suspension.

In yet another embodiment of the present invention, wherein the pharmaceutical composition manufactured is nano-suspension, which results in to enhanced in-vitro dissolution profile.

Another embodiment according to the present invention, wherein the formulated product manufactured is nano-suspension, which results in to enhanced in-vitro dissolution profile about 80% to 95%.

Additional embodiment according to the present invention, wherein the formulation manufactured is nano-suspension, which results in to enhanced bio-absorption about 40% to 90%, preferably, 90%.

In yet another embodiment of the present invention, wherein the pharmaceutical composition manufactured by number of stages in manufacturing process including homogenization, sonication, mixing and/or evaporation by spray drying.

Additional embodiment according to the present invention is that the formulated product is a stabilized homogenous suspension.

In yet another embodiment of the present invention, wherein pH of the pharmaceutical composition is in the range of 2 to 6.5, more preferably in the range of 3.0 to 4.5, most preferably around 3.8.

In another embodiment, the process comprises a step for providing Edaravone, wherein the Edaravone is contained part-A that may be prepared by mixing Edaravone with one or more pharmaceutically acceptable excipients.

Another embodiment, the process comprises a step for providing Edaravone, wherein the part-B of stabilizers may be prepared by mixing one or more pharmaceutically acceptable stabilizers.

In one embodiment, part-C means one or more pharmaceutically acceptable suspending or thickening agents.

In another embodiment, the process comprises a step for providing Edaravone, wherein the part-D may be prepared by mixing one or more pharmaceutically acceptable sweetening agents, flavoring agents and coloring agents.

In one embodiment, part-E means one or more pharmaceutically acceptable vehicle.

In another embodiment of the present invention, so as to minimize oxidation of the sensitive material it is also desirable to remove headspace oxygen and moisture or both from the sealable vessel as quickly as possible. This may be aided by, for example, purging the sealable container with a gas which is substantially oxygen-free, or substantially moisture free, or substantially oxygen and moisture free before, during or after step, or any combination thereof. Purging can be expected to reduce the oxygen level in the sealable container to a level of from about 0.5% to about 10%, typically about 5% or lower, depending on the efficiency of flushing and how quickly the container is sealed after flushing.

The gas used for purging the sealable container may be any appropriate inert gas known to those in the art, the most commonly used gases being argon, helium or nitrogen, or mixtures thereof. However, the most preferred inert gas is nitrogen.

Stability of the pharmaceutical composition of the present formulation has been achieved by controlling the total oxygen content in the drug suspension and glass bottle headspace with the use of Nitrogen. It may be important to note that the pharmaceutical formulation in the form of a suspension is typically prepared by filling contents in glass bottle or vial and then replacing the ambient air in the headspace thereof with an inert gas such as nitrogen gas, for avoiding any stability problems which may be caused during the storage. The nitrogen gas purging was carried out continuously throughout the entire compounding procedure to maintain stability of suspension, the suspension was then filled into glass bottles and glass bottles headspace was blanketed with nitrogen to achieve desirable stability through shelf life.

In another embodiment, the process comprises a step for providing above-mentioned formulation, wherein the formulation is an oral suspension that may be prepared by the steps comprising:

In one embodiment, process for preparation of an oral pharmaceutical composition as per the present invention comprising following steps:

a) dissolving anti-oxidants and/or stabilizers in purified water to prepare part-A;
b) dissolving surfactant, co-surfactant, micronized Edaravone along with permeability enhancer and anti-foaming agent to obtain a suspension;
c) dissolving suspending agent and thickening agent in above prepared suspension to provide appropriate viscosity;
d) adding sweetening agent in above-prepared suspension and mixing the same through vortex or high-speed homogenizer or mechanical or sonicated or shear stress to obtain a uniform nano-suspended formulated dosage form;
e) making-up volume of the above nano-suspension with aqueous vehicle.

Advantages of the liquid suspensions of the present invention include improved homogeneity of the suspension and ease of dispersibility of the suspension. The solids that settle in the liquid suspension of the present invention do not form a solid cake that is difficult to re-disperse. There is virtually no sedimentation of the solids in the non-reconstituted liquid suspension of this invention for a period of at least three days. This surprising feature ensures that a patient compliance.

The liquid suspensions of the present invention have a longer shelf life. Additionally, the liquid suspension, upon re-shaking, provide substantially the same effective amount of the drug as the initially prepared suspension. These features of the liquid suspensions of the present invention provide benefits to pharmacies, pharmacists, doctors and patients.

The invention will be further described with respect to the following examples; however, the scope of the invention is not limited thereby. All percentages stated in this specification are by weight, unless otherwise specified. While the present invention has been described in terms of its specific embodiments, certain modifications and equivalents will be apparent to those skilled in the art and are intended to be included within the scope of the present invention.

Example 1

TABLE 1

| Parts | Sr. No. | Ingredients | Wt. range (% w/v) |
|---|---|---|---|
| Part-A (Anti-oxidants & Stabilizer part) | 1. | Citric acid anhydrous | 0.03-0.12 |
| | 2. | Sodium bisuplhite | 0.10-0.30 |
| | 3. | L-Cysteine HCl | 0.10-0.30 |
| Part-B (Drug Part) | 4. | Edaravone (micronized) | 1.50-4.50 |
| | 5. | PEG400 | 7.00-30.00 |
| | 6. | Polyoxyetheylene sorbitan monooleate (Tween 80) | 0.20-1.00 |
| | 7. | Aerosil | 0.30-1.50 |
| | 8. | Labrafil M 1944 cs | 0.50-3.00 |
| | 9. | Black pepper oleo resin | 0.15-0.45 |
| | 10. | Simethicone 100% | 0.30-2.00 |

TABLE 1-continued

| Parts | Sr. No. | Ingredients | Wt. range (% w/v) |
|---|---|---|---|
| Part-C (Suspending agent & wetting agent Part) | 11. | Hydroxypropyl methylcellulose (E15 premium) | 0.50-4.00 |
| | 12. | Xanthan gum | 0.20-1.50 |
| Part-D (Sweetener & Flavoring agent Part) | 13. | Sucralose | 0.10-0.80 |
| Part-E (Vehicle) | 14. | Purified water | Q.s. to 100 ml |

Process for Preparation:

1. Citric acid anhydrous, sodium bisulphite and L-Cysteine HCl were dissolved in purified water to prepare part-A.
2. To the above prepared Part-A, Tween 80, PEG 400 and aerosol were slowly added to form a flocculated suspending vehicle.
3. To the suspending vehicle as prepared in step-2, micronized Edaravone was added slowly by ensuring complete dissolution of the drug.
4. To enhance the solubility of drug, a co-surfactant, Labrafil M 1944 cs was slowly added to above drug containing suspension followed by addition of Black pepper oleo resin as permeability enhancer.
5. Above all steps were performed on a stirrer and to reduce the foaming of the prepared suspension as per step-4, an anti-foaming agent Simethicone 100% was added.
6. To entrap some the drug molecule in order to maintain maintenance release just after burst release, a polymer, HPMC E15 premium was slowly mixed with above suspension prepared in step-5.
7. Further, to increase the flocculation time and by reducing the agglomeration time, a thickening agent, xanthan gum was added to the suspension as prepared in step-6.
8. Sucralose was added to the suspension prepared in step-7 and mixed through vortex or high-speed homogenizer or mechanical or sonicated or shear stress at 800-00 RPM for about 15 minutes to obtain a uniform nano-suspended formulated dosage form.
9. The nano-suspension obtained in step-8 was made up volume up to 100 ml using purified water.

Example 2

TABLE 2

| Parts | Sr. No. | Ingredients | Wt. range (% w/v) |
|---|---|---|---|
| Part-A (Anti-oxidants & Stabilizer part) | 1. | Citric Acid | 0.03-0.20 |
| | 2. | L-Cysteine | 0.10-0.40 |
| | 3. | Sodium bisulphite | 0.10-0.40 |
| Part-B (Drug Part) | 4. | Edaravone | 1.00-5.00 |
| | 5. | Tween 80 | 0.10-2.00 |
| Part-C (Suspending agent & wetting agent Part) | 6. | Hydroxypropyl methylcellulose (3 cps) | 0.25-5.00 |
| Part-D (Sweetener & Flavoring agent Part) | 7. | Sucralose | 0.10-1.00 |
| | 8. | Erythrosine | 0.20-0.40 |
| | 9. | Piperine | 0.10-0.50 |
| Part-E (Vehicle) | 10. | Purified Water | Q.s. to 100 ml |

13

Common Process for Preparation of Example-2 to Example-11

1. Edaravone was dissolved or mixed with other remaining ingredients of Part-B to form Drug part.
2. All inactive ingredients of Part-A were mixed geometrically to obtain Anti-oxidant & stabilizer part.
3. Drug part (prepared as per step-1) and Anti-oxidant & stabilizer part (prepared as per step-2) were mixed through vortex or high speed or mechanical or sonicated or shear stress to obtain mixture-1.
4. All inactive ingredients of Part-D were mixed geometrically to obtain Sweetener & flavouring agent part.
5. Similar to step-3, all ingredients of Part-C and Part-D (prepared as per step-4) were mixed along with water through vortex or high speed or mechanical or sonicated or shear stress to obtain mixture-2.
6. Mixture-1 (obtained as per step-3) and mixture-2 (obtained as per step-5) along with water were mixed through vortex or high speed or mechanical or sonicated or shear stress to obtain a suspended formulated dosage form.

Example 3

TABLE 3

| Parts | Sr. No. | Ingredients | Wt. range (% w/v) |
|---|---|---|---|
| Part-A (Anti-oxidants & Stabilizer part) | 1. | Citric Acid | 0.03-0.30 |
| | 2. | Butylated Hydroxy anisole | 0.25-0.75 |
| | 3. | Ascorbic Acid | 0.10-0.50 |
| | 4. | Butylated Hydroxytoluene | 0.20-0.80 |
| Part-B (Drug Part) | 5. | Edaravone | 1.00-5.00 |
| | 6. | Polyethylene glycol | 6.00-25.00 |
| Part-C (Suspending agent & wetting agent Part) | 7. | Hydroxypropyl methylcellulose (3 cps) | 0.25-5.00 |
| Part-D (Sweetener & Flavoring agent Part) | 8. | Sucralose | 0.10-1.00 |
| | 9. | Erythrosine | 0.20-0.40 |
| | 10. | Piperine | 0.10-0.50 |
| Part-E (Vehicle) | 11. | Purified Water | Q.s. to 100 ml |

Example 4 & 5

Table-4

| Ingredients | Wt. range (% w/v) | Parts |
|---|---|---|
| Citric Acid | 0.03-0.30 | Part-A (Anti-oxidants & Stabilizer part) |
| L-Cysteine | 0.10-0.40 | |
| Sodium bisulphite | 0.10-0.40 | |
| Edaravone | 1.00-5.00 | Part-B (Drug Part) |
| Alcohol | 5.00-40.00 | |
| Hydroxypropyl methylcellulose (3 cps) | 0.25-5.00 | Part-C (Suspending agent & wetting agent Part) |
| Sucralose | 0.10-1.00 | Part-D (Sweetener & Flavoring agent Part) |
| Erythrosine | 0.20-0.40 | |
| Piperine | 0.10-0.50 | |
| Purified Water | Q.s. to 100 ml | Part-E (Vehicle) |

Table-5

| Ingredients | Wt. range (% w/v) |
|---|---|
| Citric Acid | 0.03-0.20 |
| L-Cysteine | 0.10-0.40 |
| Sodium bisulphite | 0.10-0.40 |
| Edaravone | 1.00-5.00 |
| Alcohol | 5.00-40.00 |
| Hydroxypropyl methylcellulose (15 cps) | 0.10-3.00 |
| Sucralose | 0.10-1.00 |
| Erythrosine | 0.20-0.40 |
| Piperine | 0.10-0.50 |
| Purified Water | Q.s. to 100 ml |

14

Example 6 & 7

Table-6

| Ingredients | Wt. range (% w/v) | Parts |
|---|---|---|
| Citric Acid | 0.03-0.15 | Part-A (Anti-oxidants & Stabilizer part) |
| L-Cysteine | 0.10-0.30 | |
| Sodium bisulphite | 0.10-0.30 | |
| Edaravone | 1.00-5.00 | Part-B (Drug Part) |
| Tween 80 | 1.00-16.00 | |
| Sodium carboxymethyl cellulose | 0.10-3.00 | Part-C (Suspending agent) |
| Sucralose | 0.10-0.80 | Part-D (Sweetener & Flavoring agent Part) |
| Erythrosine | 0.20-0.40 | |
| Piperine | 0.01-0.50 | |
| Purified Water | Q.s. to 100 ml | Part-E (Vehicle) |

Table-7

| Ingredients | Wt. range (% w/v) |
|---|---|
| Citric Acid | 0.03-0.15 |
| Butylated Hydroxy anisole | 0.10-0.70 |
| Ascorbic Acid | 0.05-0.20 |
| Butylated Hydroxytoluene | 0.10-0.70 |
| Edaravone | 1.00-5.00 |
| Tween 80 | 1.00-16.00 |
| Sodium carboxymethyl cellulose | 0.10-3.00 |
| Sucralose | 0.10-1.00 |
| Erythrosine | 0.20-0.40 |
| Piperine | 0.10-0.50 |
| Purified Water | Q.s. to 100 ml |

Example 8 & 9

Table-8

| Ingredients | Wt. range (% w/v) | Parts |
|---|---|---|
| Citric Acid | 0.03-0.15 | Part-A (Anti-oxidants & Stabilizer part) |
| L-Cysteine | 0.10-0.30 | |
| Sodium bisulphite | 0.10-0.30 | |
| Edaravone | 1.00-5.00 | Part-B (Drug Part) |
| Tween 80 | 1.00-16.00 | |
| Sodium alginate | 0.20-4.00 | Part-C (Suspending agent) |
| Sucralose | 0.10-0.80 | Part-D (Sweetener & Flavoring agent Part) |
| Erythrosine | 0.20-0.40 | |
| Piperine | 0.01-0.50 | |
| Purified Water | Q.s. to 100 ml | Part-E (Vehicle) |

Table-9

| Ingredients | Wt. range (% w/v) |
|---|---|
| Citric Acid | 0.03-0.15 |
| BHA | 0.05-0.70 |
| Ascorbic Acid | 0.05-0.20 |
| BHT | 0.10-0.70 |
| Edaravone | 1.00-5.00 |
| Polyethylene glycol 500 (PEG 500) | 7.00-30.00 |
| Sodium alginate | 0.10-3.00 |
| Sucralose | 0.10-1.00 |
| Erythrosine | 0.20-0.40 |
| Piperine | 0.10-0.50 |
| Purified Water | Q.s. to 100 ml |

Example 10 & 11

Table-10

| Ingredients | Wt. range (% w/v) | Parts |
|---|---|---|
| Citric Acid | 0.03-0.15 | Part-A (Anti-oxidants & Stabilizer part) |
| L-Cysteine | 0.10-0.30 | |
| Sodium bisulphite | 0.10-0.30 | |
| Edaravone | 1.00-5.00 | Part-B (Drug Part) |
| 3-cyclodextrin | 5.00-12.00 | |
| Hydroxypropyl methylcellulose | 0.10-3.00 | Part-C (Suspending agent) |

Table-11

| Ingredients | Wt. range (% w/v) |
|---|---|
| Citric Acid | 0.03-0.15 |
| L-Cysteine | 0.10-0.30 |
| Sodium bisulphite | 0.10-0.30 |
| Butylated hydroxytoluene | 0.10-0.70 |
| Edaravone | 1.00-5.00 |
| Tween 80 | 1.00-16.00 |
| Hydroxypropyl methylcellulose (3cps) | 0.10-3.00 |

-continued

| Table-10 | | Table-11 | | |
|---|---|---|---|---|
| Ingredients | Wt. range (% w/v) | Parts | Ingredients | Wt. range (% w/v) |
| Sucralose | 0.10-0.80 | Part-D (Sweetener & Flavoring agent Part) | Sucralose | 0.10-1.00 |
| Erythrosine | 0.20-0.40 | | Erythrosine | 0.20-0.40 |
| Piperine | 0.01-0.50 | | Piperine | 0.10-0.50 |
| Purified Water | Q.s. to 100 ml | Part-E (Vehicle) | Purified Water | Q.s. to 100 ml |

Example 12

In one particular embodiment, the present invention may be prepared using following exact formula:

TABLE 12

| Parts | Sr. No. | Ingredients | Use | % w/v | mg/ml |
|---|---|---|---|---|---|
| Part-A | 1. | Citric acid anhydrous | Anti-Oxidant and Buffer | 0.05 | 0.5 |
| | 2. | Sodium Bisulphite | Preservative and stabilizer | 2 | 20 |
| | 3. | L-cysteine HCl | Anti-Oxidant and stabilizer | 1 | 10 |
| | 4. | Purified water | Vehicle | 17 | 170 |
| | 5. | Simethicone 100% | Antifoaming agent | 0.6 | 6 |
| | 6. | PEG 400 | Solubilizer, Wetting agent | 15 | 150 |
| | 7. | Polyoxyethylene sorbitan monolete (Tween 80/HLB15) | Solubilizer, Wetting agent | 0.7 | 7 |
| | 8. | Labrafil M 1944 cs | Wetting agent | 1 | 10 |
| | 9. | Edaravone (Micronized) | API | 3 | 30 |
| | 10. | Aerosil | Suspending agent | 0.5 | 5 |
| | 11. | Black pepper oleoresin | Mask the unpleasant taste | 0.3 | 3 |
| Part-B | 12. | HPMC E15 premium | Viscosity enhancer, Thickening agent | 1 | 10 |
| | 13. | Xanthan gum | Viscosity enhancer, Suspending Agent | 0.37 | 3.7 |
| | 14. | Purified water | Vehicle | 40 | 400 |
| Part-C | 15. | Sucralose | Sweetener | 0.2 | 2 |
| | 16. | Purified water (QS) | Vehicle | 17.28 | 172.8 |

Process for Preparation of Example-12

1. Micronized Edaravone was first dissolved in surfactant and wetting agent;
2. all other ingredients of part-A were geometrically dissolved in vehicle and added to above step-1 to get smooth paste or slurry;
3. the slurry was transferred to a colloid mill or a disperser or any other suitable equipment to completely wet the particles and make uniform suspension;
4. the suspending agents or flocculating agents then were dissolved in an aqueous vehicle;
5. the vehicle containing the suspending agent or flocculating agent was added to the suspension of above step-3 followed by addition of sweetener;
6. volume was made up to the final dispersion volume and filled in the vial;
7. the ambient air in the headspace of the vial with an inert gas such as nitrogen gas was flushed for avoiding the probable stability problems which may be caused during the long-term storage.

Example 13

The suspension prepared as per the present invention was subjected to check dissolution profile using USP type-II (paddle) apparatus. Here, the dissolution medium used was 0.1 N HCl and dissolution volume was 900 ml. The oral suspension prepared as per the present invention was containing 30 mg of dissolved Edaravone in 1 ml of the same. From below results, the inventors of the present invention surprisingly obtained the dissolution of the suspension not less than 98% in initial 30 minutes.

TABLE 13

| | Composition prepared as per . . . | | |
|---|---|---|---|
| Time interval | Example-1 | Example-2 | Example-12 |
| 30 minutes | 99.15 | 98.98 | 99.98 |

Example 14

The suspension prepared as per the present invention are found to be stable and following are results obtained:

TABLE 14

| Composition prepared as per . . . | Time interval | | |
|---|---|---|---|
| | Initial | After 3 months | After 6 months |
| Example-1 | 100.82 | 100.10 | 100.05 |
| Example-2 | 100.10 | 100.02 | 99.98 |
| Example-12 | 100.55 | 100.35 | 100.10 |

Above results are representative data for composition prepared as per Example-1, 2 and 12.

The compositions prepared as per the present invention are subject to animal pharmacokinetic studies to establish absorption by oral route and it is observed that the extent of absorption post oral administration is ranging from 5% to 90%.

The invention described herein comprises in various objects as mentioned above and their description in relation to characteristics, compositions and process adopted. While these aspects are emphasised in the invention, any variations of the invention described above are not to be regarded as departure from the spirit and scope of the invention as described.

The above-mentioned examples are provided for illustrative purpose only and these examples are in no way limitative on the present invention.

The invention claimed is:

1. A pharmaceutical composition, comprising an oral suspension, wherein the oral suspension comprises:

edaravone or a pharmaceutically acceptable salt thereof, in a concentration of at least 2% w/v; and the following pharmaceutically acceptable excipients;

a. an antioxidant, in a concentration of not more than 3.5% w/v;

b. a wetting agent, in a concentration of not more than 20% w/v;

c. a suspending or thickening agent, in a concentration of not more than 2% w/v;

d. an anti-foaming agent, in a concentration ranging from 0% w/v to 1% w/v;

e. a sweetening, coloring, or flavouring agent, in a concentration ranging from 0% w/v to 0.5% w/v; and f. a vehicle, in a concentration of at least 65% w/v;

wherein each concentration is based on the total amount of the formulation;

wherein Edaravone is in a micronized form in the oral suspension; and wherein the particle size $D_{100}$ of the micronized form of Edaravone is less than 8000 nm.

2. The pharmaceutical composition as claimed in claim 1, wherein the antioxidant is selected from the group consisting of citric acid anhydrous, sodium bisulphite, L-cysteine HCl, Butylated hydroxytoluene, butylated hydroxy anisole, ascorbic acid, and mixtures thereof.

3. The pharmaceutical composition as claimed in claim 1, wherein the wetting agent is selected from the group consisting of PEG 400, PEG 500, polyoxyethylene sorbitan monooleate (Tween 80/HLB15), an oleoyl polyoxyl-6 glyceride, β-cyclodextrin, alcohol, polyethylene glycol and mixtures thereof.

4. The pharmaceutical composition as claimed in claim 1, wherein the suspending or thickening agent is selected from the group consisting of HPMC E15 premium, Hydroxypropyl methylcellulose (3 CPS), Hydroxypropyl methylcellulose (15 CPS), Sodium alginate, Xanthan gum, fumed silica, Sodium carboxymethyl cellulose and mixtures thereof.

5. The pharmaceutical composition as claimed in claim 1, wherein the anti-foaming agent is selected from the group consisting of simethicone, dimethicone, and mixtures thereof.

6. The pharmaceutical composition as claimed in claim 1, wherein the sweetening or flavouring agent is selected from the group consisting of black pepper oleoresin, sucralose, erythrosine, piperine, and mixtures thereof.

7. The pharmaceutical composition as claimed in claim 1, wherein the oral suspension comprises:

Edaravone or a pharmaceutically acceptable salt thereof, in a concentration of at least 25 mg/ml;

water, in a concentration of at least 75% w/v; and the following pharmaceutically acceptable excipients:

citric acid anhydrous in an amount of up to 0.05% w/v;

sodium bisulphite in an amount of up to 2% w/v;

L-cysteine HCl in an amount of up to 1% w/v;

simethicone in an amount of up to 0.6% w/v;

PEG 400 in an amount of up to 15% w/v;

polyoxyethylene sorbitan monooleate in an amount of up to 0.7% w/v;

oleoyl macrogol-6 glyceride in an amount of up to 1% w/v;

fumed silica in an amount of up to 0.5% w/v;

black pepper oleoresin in an amount of up to 0.3% w/v;

HPMC in an amount of up to 1% w/v;

xanthan gum in an amount of up to 0.37% w/v; and sucralose in an amount of up to 0.2% w/v;

wherein Edaravone is in a micronized form in the oral suspension; and the particle size D100 of the micronized form is less than 8000 nm.

8. The pharmaceutical composition as claimed in claim 1, wherein the oral suspension is produced by a process comprising:

mixing micronized Edaravone with the wetting agent to form a first mixture;

adding the vehicle to the first mixture to form a slurry; and transferring the slurry to a colloid mill to make a uniform suspension.

9. The pharmaceutical composition as claimed in claim 1, wherein the oral suspension is produced by a process comprising:

mixing micronized Edaravone with the wetting agent to form a first mixture, wherein the wetting agent is PEG 400, polyoxyethylene sorbitan monooleate, oleoyl macrogol-6 glyceride, or a mixture thereof;

adding the water to the first mixture to form a slurry; and transferring the slurry to a colloid mill to make a uniform suspension.

* * * * *